United States Patent [19]

Khan

[11] Patent Number: 4,968,312

[45] Date of Patent: Nov. 6, 1990

[54] DISPOSABLE FECAL COMPARTMENTING DIAPER

[76] Inventor: Sarbuland Khan, 1539 N. Alexandria Ave., #304, Los Angeles, Calif. 90027

[21] Appl. No.: 332,770

[22] Filed: Apr. 3, 1989

Related U.S. Application Data

[62] Division of Ser. No. 201,893, Jun. 3, 1988, Pat. No. 4,834,737.

[51] Int. Cl.$^5$ .............................................. A61F 13/16
[52] U.S. Cl. ................................ 604/388.1; 604/385.2
[58] Field of Search ................... 604/385.1, 385.2, 350, 604/351, 355, 392, 393, 394, 395

[56] References Cited

U.S. PATENT DOCUMENTS

| | | | |
|---|---|---|---|
| 584,204 | 6/1897 | Bowles | 604/397 |
| 2,529,999 | 11/1950 | Chambers | 604/351 |
| 2,532,029 | 11/1950 | Medoff | 604/394 |
| 3,103,930 | 9/1963 | Collett et al. | 604/355 |
| 3,182,661 | 5/1965 | Ribeiro et al. | 604/395 |
| 3,424,160 | 1/1969 | Koornwinder et al. | 604/393 |
| 3,890,973 | 6/1975 | Davis et al. | 604/392 |
| 4,285,342 | 8/1981 | Mesek | 604/375 |
| 4,381,782 | 5/1983 | Mazurak et al. | 604/368 |
| 4,578,072 | 3/1986 | Lancaster | 604/385.2 |

Primary Examiner—C. Fred Rosenbaum
Assistant Examiner—Mark O. Polutta
Attorney, Agent, or Firm—Albert O. Cota

[57] ABSTRACT

A disposable diaper which has a liquid impervious back sheet (30) to which absorbent padding (38) is attached each having a passage therethrough with a cover (64) enclosing this hole (32) in the back sheet. A pull through insert (42) is juxtapositioned on the padding and a bag (66) is attached to the insert and around this opening (40). A wiping and cleansing action is accomplished prior to removal of the soiled diaper by breaking the cover on the hole and grasping the bag, to which a loop (68) is attached and pulling the insert through the passage while simultaneously using the bag as a glove to accomplish the wiping action. The insert is completely contained within the bag and enclosed by a tie (70). In other embodiments, a conformal liner (74) is positioned over the insert or padding and contains an aperture (76) through which fecal matter passes separating it from the wearer into an area therebetween and alternatively a fully contoured padding contains an aperture below which may be positioned the insert for pull-through wiping.

4 Claims, 4 Drawing Sheets

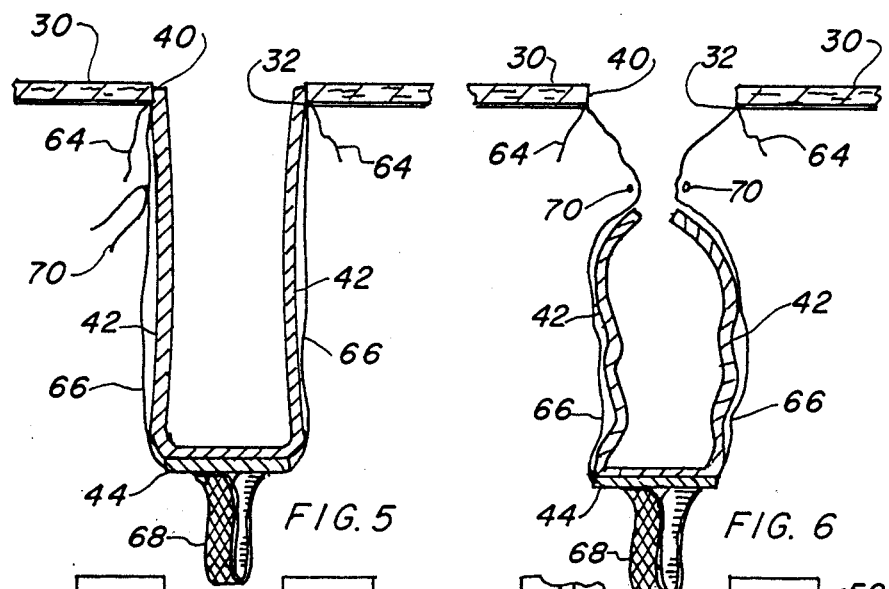

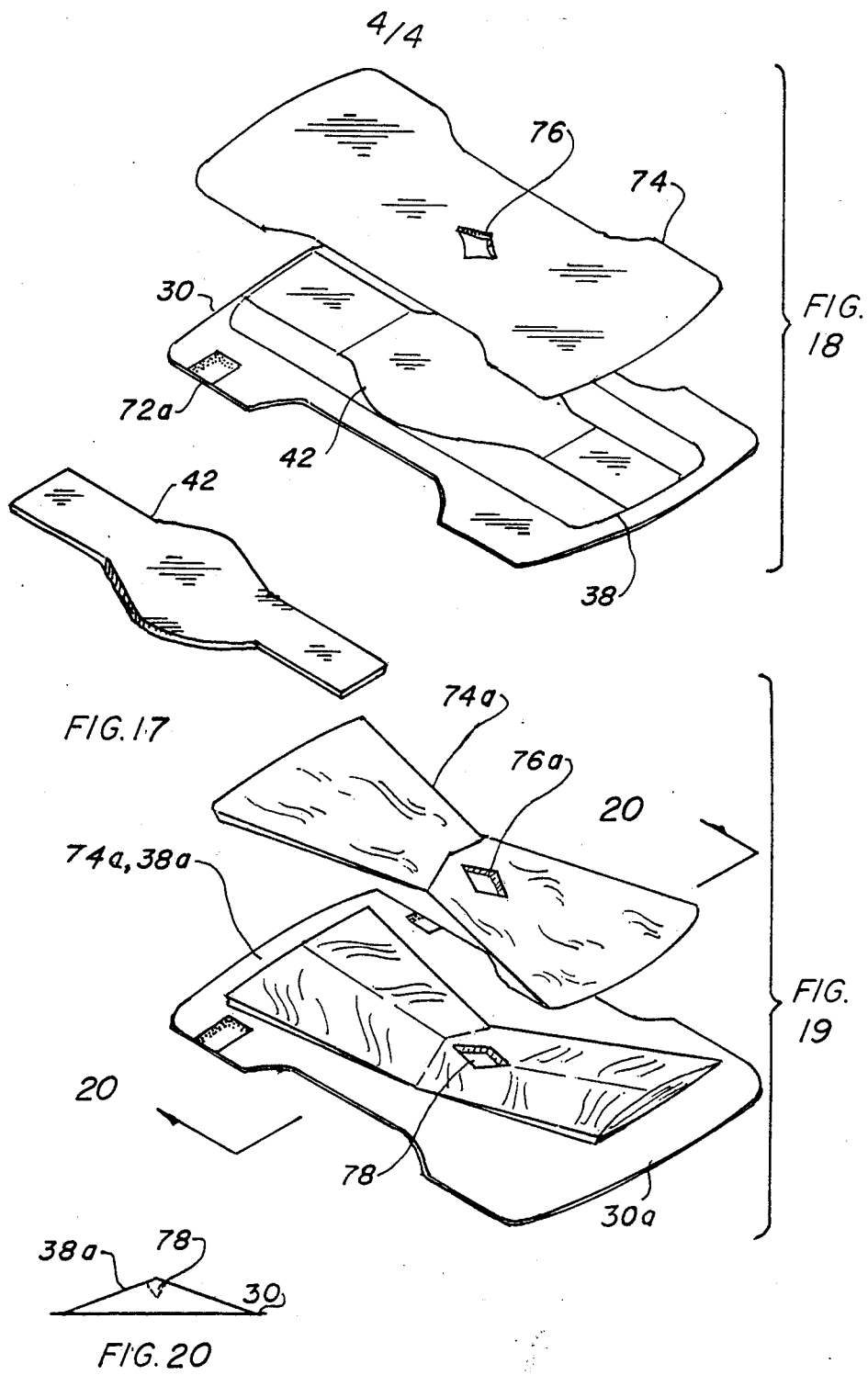

DISPOSABLE FECAL COMPARTMENTING DIAPER

CROSS REFERENCE TO RELATED APPLICATION

This application is a divisional application of application Ser. No. 07/201,893 filed June 3, 1988 now U.S. Pat. No. 4,834,737.

TECHNICAL FIELD

The invention pertains to the general field of diapers and more particularly to disposable diapers having a combination structural/method that allows the rectal area to be cleaned while the excrement is being bagged in a sanitary pull-through bag.

BACKGROUND ART

Since the introduction of the cloth diaper, many attempts have been made by parents, as well as manufacturers, to improve the utility and basic folding configuration of the diaper. Some of the early modifications included, adding a loose liner around the area of the anus, placing a gathering material in the diaper's inner edge to hold the material tight against the legs of the human torso and adding snaps or hooks to eliminate the need for using safety pins to hold the diaper in place. None of the above prevented "diaper rash" nor the ability to adequately hold and contain urine and feces.

Secondary diaper design considerations, primarily implemented by diaper manufacturers, included the use of paper diapers having a combination of absorbent materials, a two dimensional contour shape and an inner leg gathering material. Some of the current and prior art diapers have also included various forms of integral disposal systems However, none of the prior art patents disclose a diaper that collects urine and feces into an attached pull-through resilient bag that while placing the excrement into the bag, allows the baby's buttocks and rectal area to be cleaned.

A search of the prior art did not disclose any patents that read directly on the claims of the instant invention however, the following U.S. patents were considered related:

| U.S. Pat. No. | INVENTOR | ISSUED | |
| --- | --- | --- | --- |
| 4,604,096 | Dean, etal | 5 August | 1986 |
| 4,578,073 | Dysart, etal | 25 March | 1986 |
| 4,560,380 | Tharel | 24 December | 1985 |
| 3,776,233 | Schaar | 4 December | 1973 |
| 3,369,545 | Wanberg | 20 February | 1968 |
| 19,418 | Hall | 23 February | 1858 |

The Dean et al and Wanberg patents disclose diapers including integral disposal systems. The Dean et al is complicated and must be removed and handled before it is bagged. Therefore, it does not alleviate the problem of fowl smell and sight of the feces. The Wanberg patent is designed to be thrown away after the diaper is soiled. The entire diaper is wrapped-up after use and placed in a pouch that is part of the diaper.

The Tharel and Hall patents disclose diapers having urine receiving receptacles. The Tharel patent is a mini-diaper that compensates for reduction in size by incorporating extra space in added pleats or passages for the retention of soil. The Hall patent is very complicated and not practical. The design includes an air cushion sized to fit the posterior of an infant and includes an opening in the center. The cushion is combined with a cloth and a bag of waterproof material such that when the cushion is attached to the body, the excrement and urine is discharged through the opening in the cushion and into the bag where it will be retained The Dysart et al and Schaar patents disclose only general contoured diapers and inserts. The Dysart et al patent discloses a waste-containment garment comprising a disposable waste-containment insert secured to the insert inside a non-elasticized over-garment such as a disposable diaper. This device is not cost-effective. The Schaar patent consists of an imperfect contourable diaper which includes a pleated fluid-pervious cover sheet and a fluid-pervious back sheet secured to each other and to the lateral and longitudinal edges of the diaper. This diaper is contourable upon stretching and will only maintain this contour as long as a pulling force exists.

DISCLOSURE OF THE INVENTION

The disposable diaper is designed for the baby's comfort and to significantly minimize the unpleasantness associated with directly removing and wiping excrement and its accompanying odor. The diaper also minimizes diaper rash episodes by allowing only a minimum quantity, if any, of urine and feces to directly contact the wearer's skin. The inventive diaper functions by allowing the excrement to be collected in a diaper-integral resilient pull-through bag. The bag is designed so that as the excrement is being collected into the bag, the baby is simultaneously being wiped clean.

The diaper design utilizes two principles to achieve the above described results—the three-dimensional contour principle and the pull-through principle.

The contour principle is based on the fact that feces pass between the wearer's skin and a regular diaper through natural body contours. These contours are located in the front between the legs and in the rear between the baby's buttocks—thus, a natural channel is provided without obstructing the passage of the feces regardless of the baby's position.

The contour principle, as applied to the instant invention, utilizes either a thin lining or a thinly padded lining that form a three-dimensional barrier or "second skin" between the skin and the feces. This second skin is made to fit firmly against the wearer's body, to follow the natural contours of the body and includes an anal opening that allows the feces to pass through. The lining in its preferred embodiment is an element of the diaper and is located on top of the diaper's main pad. However, as a second embodiment, the lining may be totally separate from the main diaper.

The contoured diaper assembly works especially well on younger babies who do not yet stand or walk. This is so because with older babies who stand, their legs are closer together which tends to close the anal opening.

The pull-through principle is based on the fact that more often than not, the feces are deposited in the diaper within a localized area. When the feces pass through, the anal opening in the "second skin", they normally come to rest upon the localized area on a thinly padded second lining that is located on the inside surface of a regular type diaper. Around the feces collection area, the diaper has an opening that is attached internally to a resilient pull-through bag. Through this opening is inserted a hand that grasps the bag which is internally attached to the insert. The bag is then slowly pulled through the opening, pulling the feces through and the hand is simultaneously manipulated so that the baby's buttocks and anus are both cleansed.

In view of the above disclosure, it is the primary object of the invention to provide a comfortable diaper that allows excrement to be easily removed, as described above, while at the same time allowing the baby's buttocks to be cleansed In addition to the primary object it is also an object of the invention to have a diaper that:

totally or significantly reduces any physical and eye contact with baby feces, totally or significantly reduces diaper rash, totally or significantly reduces the unpleasant odor of excrement, allows a more sanitary disposal of the used diaper, allows the baby's buttocks to be cleansed at the same time the feces are being removed thus, totally eliminating or reducing the amount of direct hand wiping that is presently required with conventional diapers.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 5 is a cross-sectional view taken along lines 5—5 of FIG. 1 illustrating the diaper having the insert fully pulled out of the hole and opening.

FIG. 6 is a cross-sectional view taken along lines 6—6 of FIG. 1 illustrating the diaper having the insert fully pulled out of the hole and opening and the bag enclosing means optionally tied around the bag.

FIG. 7 is a partial plan view of the front end of the insert illustrating parallel slots therein.

FIG. 8 is a partial plan view of the front end of the insert illustrating the moisturized lotion area.

FIG. 9 is a partial plan view of the front end of the insert illustrating the integral ridge.

FIG. 10 is a partial plan view of the front end of the insert illustrating a cleaning agent contained within a breakable plastic film.

FIG. 11 is a partial cross-section of the invention as in FIG. 1 illustrating the slits in the padding to retain the insert.

FIG. 12 is a plan view of an insert removed from the invention for clarity illustrating its shape.

FIG. 13 is a plan view of an insert removed from the invention for clarity illustrating the overall shape.

FIG. 14 is a plan view Of an insert removed from the invention for clarity illustrating the overall shape.

FIG. 15 is a plan view of an insert removed from the invention for clarity illustrating the preferred overall shape.

FIG. 17 is a partial isometric view of the replaceable absorbent padding completely removed from the invention for clarity.

FIG. 18 is a partial isometric view of the second embodiment of the invention with the elastized conformal liner exploded from the diaper for clarity.

FIG. 19 is a partial isometric view of the second embodiment as above with the cavity illustrated in the central portion.

FIG. 20 is a cross-sectional view taken along lines 20—20 of FIG. 19 illustrating the cavity in cross-section.

BEST MODE FOR CARRYING OUT THE INVENTION

The best mode for carrying out the invention is presented in terms of a preferred, second and third embodiments. The first embodiment is similar to the second and the second is similar to the third. The second embodiment adds a contoured liner and the third replaces the pull-through capability with a combination of a padding cavity and the liner, where the padding is elastized against the back sheet.

The preferred embodiment, as shown in FIGS. 1 through 16 is comprised of a liquid impervious back sheet 30 configured generally in a rectangular shape with the longitudinal sides slightly curved inwardly in the central portion. The back sheet 30 further contains a longitudinally off center hole 32 whose circumference is tangent to the center line in FIG. 1 and is preferably round, for better rigidity, however, any shape will be operable. The back sheet 30 being impervious to fluids is of a width capable of being overlapped on the sides when wrapped around a human torso. Leg cuffs 34 are integrally formed into the sheet by a plurality of elastic strands 36 that gather the material displacing the longitudinal sides creating a tight fit around the wearer's legs.

Figure 1:
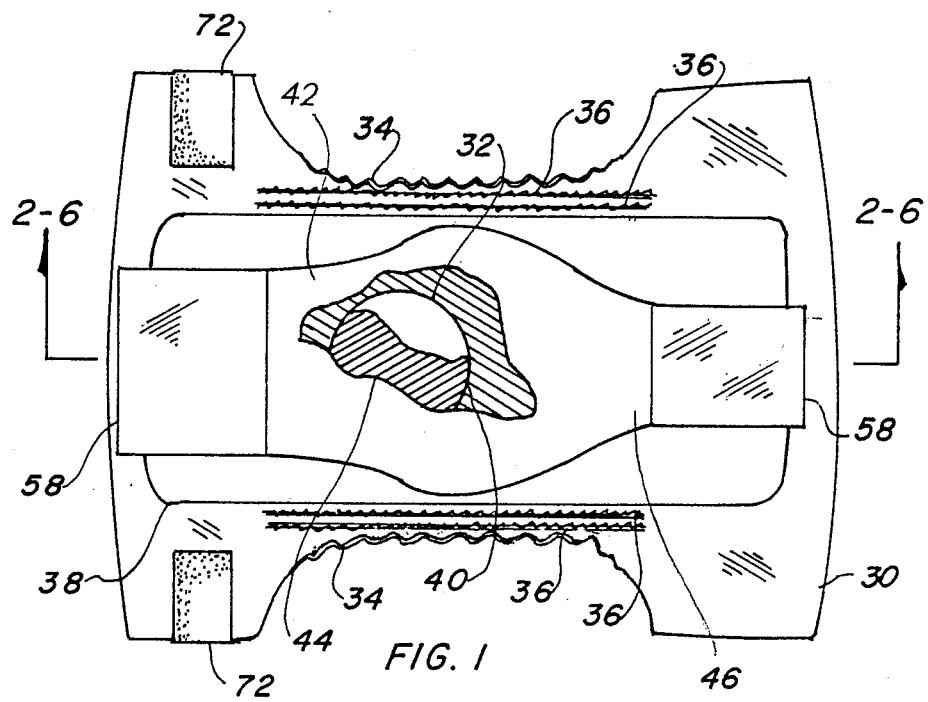
FIG. 1 is a plan view of the preferred embodiment showing the insert and circular pad partially cut away for clarity.
Figure 16:
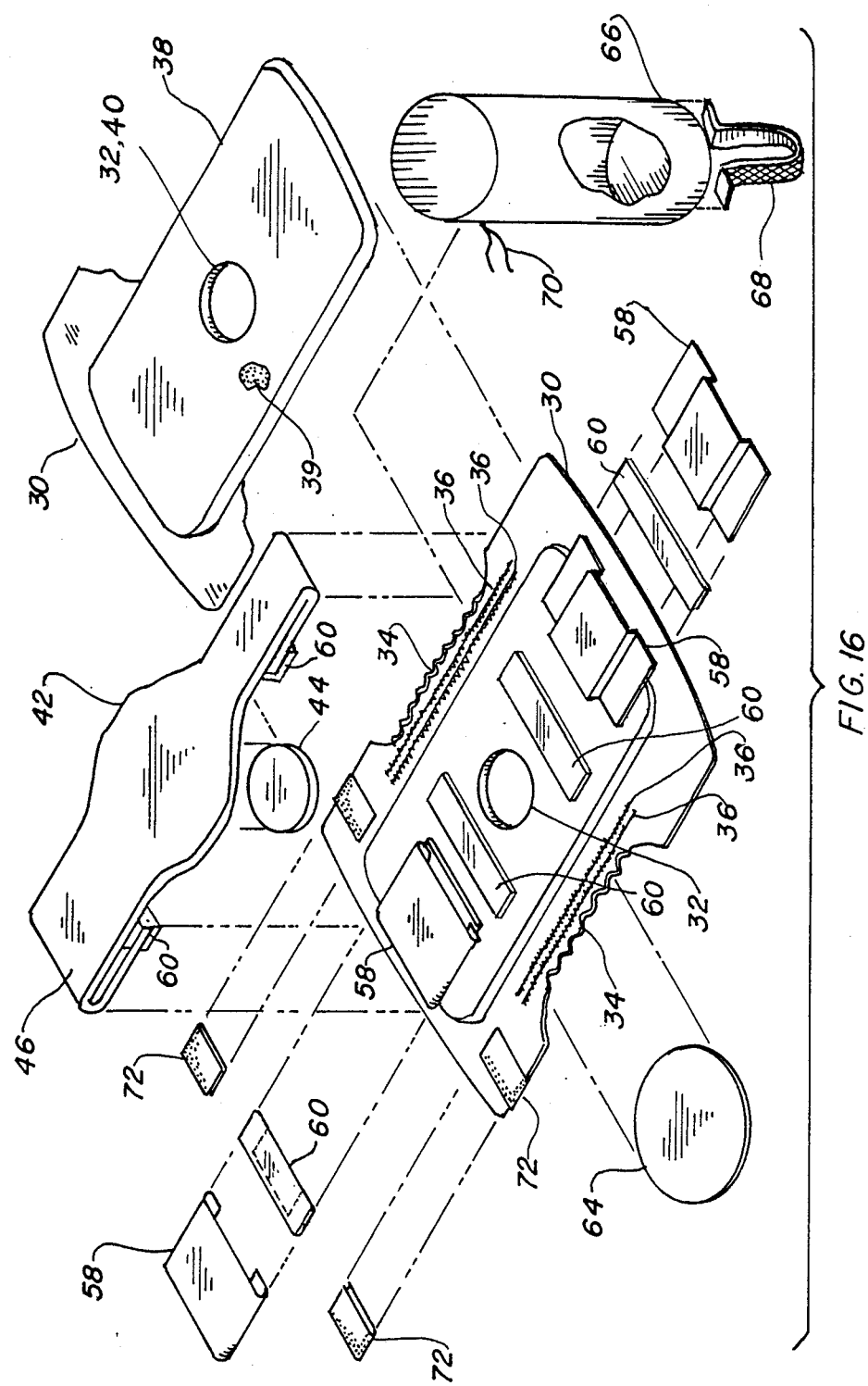
FIG. 16 is an exploded view of the preferred embodiment.

The diaper utilizes absorbent padding 38 having an opening 40 in the middle that is aligned with the hole 32 in the back sheet 30. The padding 38 is compressed sufficiently to maintain its integral form by gluing, bonding, stitching or the like. The padding is disposed upon the back sheet 30 in a generally centralized position as best illustrated in FIGS. 1 and 16 and is attached thereunto by means well known in the art. In a variation of the attachment of the padding to the back sheet, the padding 38 may be replaceable as illustrated in FIG. 16 with pressure sensitive adhesive means or the like on one or more of the sides to attach the elements together in a removable manner.

Further, the padding 38 may contain dehydrated or anhydrous gelatin crystals or granules 39 that are intermixed within the fibers allowing human liquid waste to react changing it into a viscous semi-liquid thereby retaining it within the padding. The padding material may be any type well known in the art and commonly used for this utility.

A semi-absorbent and semi pervious pull-through insert 42 is juxtapositioned contiguously onto the padding 38 almost covering the rear section of the padding completely but quite tapered toward the front. The insert 42 has a shape that is generally smaller than the padding in width at the back and in the preferred mode, considerably smaller in the front but longer on each end allowing it to be folded over. The shape may infinitely vary with some of these configurations illustrated in FIGS. 12–15. While FIG. 15 is the preferred embodiment, the other variations may be used depending upon type of materials used, relative sizes to diaper itself and the cleaning mode used. The insert 42 is formed of the same or similar materials, used in the padding with the absorbent feature being of prime consideration in its selection. Dehydrated gelation crystals 39 may not be used to improve the liquid absorbing qualities.

Preferably, a circular pad 44 is used that is slightly smaller in size then the hole 32 in the back sheet but tightly fitting the opening 40 in the diaper padding and being approximately the same thickness as the diaper pad such that the circular pad 44 will fit directly into the opening 40 and become planar with the padding 38. The material used is the same as the diaper pad itself, also the attachment means to the insert.

The insert 42 may have a top facing 46 of soft non-absorbent but fluid pervious material isolating the insert from contact with the wearer for the purpose of gaining the sensory perception of dryness.

In order to make an allowance for a softer surface of the ends of the insert 42 where contact is made with the tender parts of the wearer's body, a series of parallel slits 42 aligned with the closest end are optionally provided. Optionally, both ends may have a fluffy padding, compared to center which is relatively dense or compressed like the main diaper pad. Also, if treating males separately, the padded area coincidental with male genitals may be compressed, or formed, into a cup shape and a tapered, or slitted and tapered or fluffed front section pull-through material may be used.

As the insert 42 is in direct contact with the wearer or with only the liner 46 inbetween, the portion near the end next to the front of the wearer or both front and rear end sections may contain protective elements such as a non-evaporating moisturizing lotion 50 imbedded into the material or a cleansing agent 52 or the like. For example, the cleansing agent 52, as shown in FIG. 10, is contained within breakable plastic film sleeves 54 disposed on the surface position so as to break when the insert 42 is rubbed across the body while being removed when the configuration is such that one or both ends reside under the diaper pad. Further, in order to prevent waste from remaining on the wearer, a ridge 56 is integrally formed into the surface opposite the front end conforming to the wearer's buttocks. This ridge is best illustrated in FIG. 9 and may continue along the entire surface in contact with the wearer in that region of the body, or exist in the latter half of that region.

In functional operation, the insert 42 is pulled through the hole 32 and the opening 40 while the diaper is still worn in its first short stage of pulling through the fecal matter, and the second stage of creating a wiping action in the process of using the bag as a glove from one side of the bag while pulling and wiping with the remaining material of the pull through insert.

In order to allow sufficient area to completely clean the wearer, both ends of the insert 42 are folded under with tension means provided to hold the insert in place and create a controlled functional resistance. The tension means are characterized by a pocket 58 on each end that is attached to the absorbent padding 38 on at least two sides or optionally on three with the open end in any case toward the middle of the diaper.

The pockets 58 (and pouch 60 below) may be cut into the liner or externally attached and made of any material suitable for the application with a soft non-absorbent but liquid permeable substance such as used for the top liner 46 being preferred. The ends of the insert are further retained by a slide stop pouch 60 attach end that is disposed under the pocket 58 and attached on three sides with the open side facing the pocket 58. This arrangement allows the insert 42 to be unfolded at the top while moving downward assuring a flat surface to create a full wiping action across the bottom instead of the folded end retaining its configuration during the process.

Another embodiment of the tension means, is lieu of the pockets 58 and pouch 60, is illustrated in FIG. 11 and consists of a pair of slots 62 in the padding 38 through which the insert 42 penetrates. This arrangement allows the wiping action to take place while eliminating the movement over tender parts of the wearer's body particularly the males genital area, and allows plastic contained wipes to be used.

A liquid impervious hole cover 64 is either attached to or integral with the back sheet 30. If it is attached, the material may be of a different composition than the back sheet such as plastic film or at least a substance that is easily torn or broken allowing access into the interior of the diaper.

If the cover is integrally formed, a thinner area or perforations or the like may be employed. At any rate, the cover 64 functions to enclose the bottom of the diaper while allowing accessibility to elements thereunder.

A resilient bag 66 of thin plastic film such as polyvinyl chloride or the like is attached on the open end around the hole 32 in the back sheet 30 in a liquid tight manner. The closed end of the bag 66 is attached to the pull through insert 42 at the circular pad 44 in particular, if one is utilized. The bag 66 creates a chamber between the hole cover 64 and the insert 42 allowing access without physically touching the interior elements of the diaper.

Grasping means in the form of a loop 68 is affixed to the closed end of the bag 66 to allow easy gripping when pulling the insert 42 through the opening 40 and hole 32. The bag 66 being attached to the insert 42, is pulled out by the loop 68 and enclosing means in the form of a string or ties 70 are optionally provided on the outside surface near the attached end. The ties encompass the bag 66 allowing it to be gathered together and tied off.

In order to hold the diaper onto the wearer, attaching means well known in the art are utilized. Any type of fastener may be employed, however, pressure sensitive adhesive tabs 72 are preferred. These tabs 72 are disposed on opposite corners on the back of the diaper and have a peelable cover allowing them to be stripped from part of the tab 72 and attached to the front of the diaper changing the shape of the diaper from flat to an arcuate configuration fitting around the wearer's torso with the elastized leg cuffs gathering around the legs to complete the closure.

The second embodiment shown in FIGS. 17 and 18 includes all of the elements of the preferred embodiment plus the addition of an elastized conformal liner 74 of non-absorbent and soft material that fits three dimensionally the contour of the wearer's body snugly. If desired, the entire liner may be made of stretchable material and preferably may also be thinly padded similar to the pull through. When the diaper is applied, the liner 74 conforms to a perfect body likeness rather than the actual shape of the diaper due to its elastic nature.

This fit is accomplished by having the liner 74 which in its unworn (unstretched) size is smaller than the diaper peripherally attached to the back sheet 30 causing it to stretch as required. An aperture 76 is centrally located in the liner in such a position as to be aligned with the wearer's anus. This location allows fecal material to penetrate the aperture 76 and collect in the area between the liner 74 and the insert 42 separating it from the wearer making cleansing easier and helping further to prevent annoyances to the wearer's skin. The aperture 76 in the liner 74 may be of any shape such as round, square, serrated as shown in FIGS. 18 and 19 and may be plain around the edge or gathered with elastized strands or thread. A number of configurations are workable including strips of elastic around the edges of a round, diamond or elliptical hole pattern. The only limitation is that the opening be in the proper location and that it fit tightly around the periphery of the anus by the ability of the lining to perfectly contour in three-dimensions.

In usage, both the preferred and the second embodiment function in the same manner. The diaper is put on the wearer in the normal manner, however, extra skin protection is included in the second embodiment.

When the diaper is soiled by fecal matter and ready to be removed, cleansing and wiping is accomplished by slightly spreading the wearer's legs apart, when the wearer is lying down or in a standing position. The pressure on the buttock is normally alleviated in the standing position, however, in smaller infants, pressure is alleviated by lifting the back sheet 30 slightly, and tearing the hole cover 64 with a outward pull. One hand is then placed around the hole 32 forming a wide semi-circle with the thumb and forefinger and the other hand grasps the loop 68 that has been exposed after tearing the cover 64 open.

Figure 2:
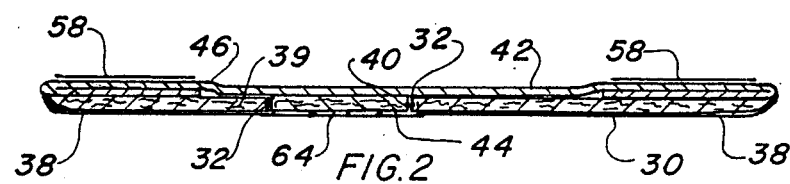
FIG. 2 is a cross-sectional view taken along lines 2—2 of FIG. 1 illustrating the diaper in the fully closed condition.
Figure 3:
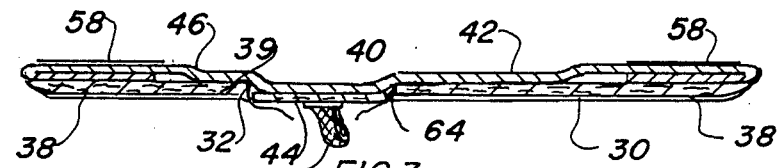
FIG. 3 is a cross-sectional view taken along lines 3—3 of FIG. 1 illustrating the diaper with the hole cover removed exposing the gripping loop.
Figure 4:
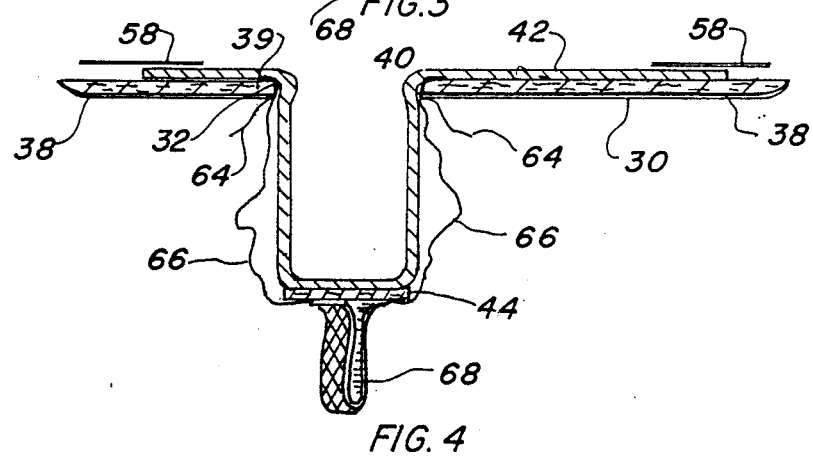
FIG. 4 is a cross-sectional view taken along lines 4—4 of FIG. 1 illustrating the diaper having the insert partially pulled out of the hole and opening.

The removal procedure and wiping action, without the hand depicted, is pictorially illustrated in sequence in FIGS. 2 through 6 with FIG. 2 showing the diaper in cross section prior to removal.

When the insert 42 is completely enclosed in the bag 66 that has unfolded in the process, the string or ties 70 are wrapped around the bag at the upper end and tied off to completely isolate the insert with its accompany waste from both sight and smell and the balance of the diaper may be removed in the normal manner.

The third embodiment is illustrated in FIGS. 19 and 20 and includes a similar back sheet 30a except the hole 32 is eliminated and likewise, the absorbent padding 38a has the opening 40 deleted.

It will be noted that while the padding 38a is basically the same in material and function, it contains a tight contour shape with an aperture that is positioned for the anus in the center thus, creating a cavity 78 that collects body waste from the wearer. The conformal liner 74a, as shown in FIG. 19, integrally attached to the padding 38a and has the same aperture 76a, serving the purpose of isolating the fecal material from the wearer. Again, identical attaching means are employed in the form of tabs 72a as previously described.

The improvement of the third embodiment lies in the ability of the diaper to isolate the fecal material into the cavity 78 and protect the wearer therefrom by the padding 38a and the liner 74a. The function and application of the diaper otherwise is the same as prior art therefore no special procedures are required for its removal.

While the invention has been described in complete detail and pictorially shown in the accompanying drawings it is not to be limited to such details, since many changes and modifications may be made in the invention without departing from the spirit and the scope thereof. For example, the diapers can be made with a padding liner having slit located longitudinally on each side of the diaper hole. These slits create a tension means on one side and provide a slide stop on the other for the insert. Additionally, the diapers can be made of biodegradable material. Thus, when the diapers are disposed, the material is broken down into innocuous products. Hence, it is described to cover any and all modifications and forms which may come within the language and scope of the claims.

What is claimed is:

1. A disposable waste-containing diaper comprising:
   (a) a liquid impervious back sheet of a generally rectangular shape having elastized leg cuffs integral thereunto of a shape to fit a human lower torso region when overlapped together on the wearer's sides,
   (b) an absorbent padding that is elastized relative to said backsheet and having a three-dimensional contour and a hole in the center thereof such that a cavity is created between the backsheet an the padding for collecting waste from the wearer through the hole,
   (c) a liner of non-absorbent soft material following the contour of the wearer's body having an aperture centrally located therein integrally attached to said absorbent padding, and
   (d) attaching means on the back sheet at the overlapping sides to hold he diaper around the waist of the wearer when the diaper is applied to the wearer changing shape from a generally planar shape to an arcuate configuration responsive to the elastized leg cuffs of said back sheet.

2. The diaper as recited in claim 1 wherein said aperture further comprises an elastized periphery allowing the opening to expand when waste material is passing therethrough.

3. The diaper as recited in claim 1 wherein said diaper is made of biodegradable material.

4. The diaper as recited in claim 1 wherein said three-dimensional contour is extendable the full length of the diaper.

* * * * *